United States Patent [19]
Sarstedt

[11] 4,314,570
[45] Feb. 9, 1982

[54] CAPILLARY RECEPTACLE

[76] Inventor: Walter Sarstedt, 5223 Nümbrecht/Rommelsdorf, Fed. Rep. of Germany

[21] Appl. No.: 178,908

[22] Filed: Aug. 18, 1980

Related U.S. Application Data

[63] Continuation of Ser. No. 960,249, Nov. 13, 1978, abandoned.

[30] Foreign Application Priority Data

Nov. 18, 1977 [DE] Fed. Rep. of Germany ....... 2751503

[51] Int. Cl.³ .................... A61B 10/00; G01N 1/10
[52] U.S. Cl. ............................. 128/763; 73/864.02; 422/102
[58] Field of Search ............. 128/760, 762, 763, 764; 73/425.4 P, 864.02; 422/100, 102, 104

[56] References Cited

U.S. PATENT DOCUMENTS

| | | | |
|---|---|---|---|
| 3,141,336 | 7/1964 | Oates | 222/207 |
| 3,623,475 | 11/1971 | Sauz et al. | 128/762 |
| 3,718,133 | 2/1973 | Perry et al. | 422/102 X |
| 3,926,521 | 12/1975 | Ginzel | 128/763 X |
| 4,007,639 | 2/1977 | Haeckel et al. | 73/864.01 |
| 4,024,857 | 5/1977 | Blecher | 128/763 |
| 4,210,156 | 7/1980 | Bennett | 128/763 X |

*Primary Examiner*—Michael S. Marcus
*Attorney, Agent, or Firm*—Browdy and Neimark

[57] ABSTRACT

A capillary receptacle for the extraction and storage of blood, which receptacle features the improvement that an insert is provided for the receptacle, said insert having a cylindrical main portion inserted into the opening portion of the receptacle and a short funnel-shaped portion adjacent thereto, the tip of which has such a small inner diameter that blood externally thereof is drawn in by capillary action, whereas the main portion has such a large inner diameter that the entering blood is able to freely flow off.

11 Claims, 8 Drawing Figures

CAPILLARY RECEPTACLE

This is a continuation of application Ser. No. 960,249, filed Nov. 13, 1978, now abandoned.

This invention relates to a capillary receptacle for the extraction and storage of blood.

Receptacles for storing blood, in particular in the form of small tubes closed at one end and consisting of glass or a preferably transparent plastic material are conventional and serve to store the blood extracted by means of a special blood extraction device.

It is furthermore known to obtain minor quantities of blood in that a finger tip or an ear lobe of a patient is punctured and the outflowing blood is drawn with a capillary of glass or plastic which is immerged into the outflowing blood with its one end.

Also, such narrow glass capillaries have been placed into the bore of a plug for a receptacle, the plug being provided with a second bore for a pressure equalization. This device on the one hand has the disadvantage that because of the axial length of the plug stringently a capillary must be used which has a length of about 1 to 2 cms or more. In this capillary a considerable amount of blood is retained, provided, it is not specially blown empty, and this quantity is lost for testing. A blowing-out, however, is difficult to perform under sterile conditions and requires a further operation.

Also, after removing the plug provided with bores and provided with the glass capillary, a new plug must be used for closing the receptacle, and this plug increases the cost of the device further.

Finally, it is also known to enlarge such a capillary at its rearward end and to apply it to the extraction site in such a way that the blood drawn by the tip by a capillary effect then flows into the rearward, enlarged portion. It is possible with such a funnel-shaped enlarged capillary to extract a somewhat larger quantity of blood than possible with the capillaries cylindrical throughout.

In these conventional capillary receptacles, there was a more narrow intermediate portion between the tip with the capillary bore and the rearward, enlarged portion, in which intermediate portion the blood cohered as a result of the capillary effect as a self-contained column and did not detach from the wall. This brought about the disadvantage that the blood drawn by the capillary tip could not flow off rapidly.

An object of this invention is to provide a capillary receptacle operating on the above mentioned principle which permits a simple and clean removal of even larger quantities of blood flowing from an injection site by a capillary effect and a storing of this blood in a virtually closed receptacle which may then subsequently be closed completely tightly for a further storing or for dispatching.

According to the invention, the teaching of claim 1 is provided. Furtherances of the invention result from the subclaims.

The invention is explained in closer detail hereinafter in embodiments by way of example in referring to the drawings: Therein:

Figure 1:
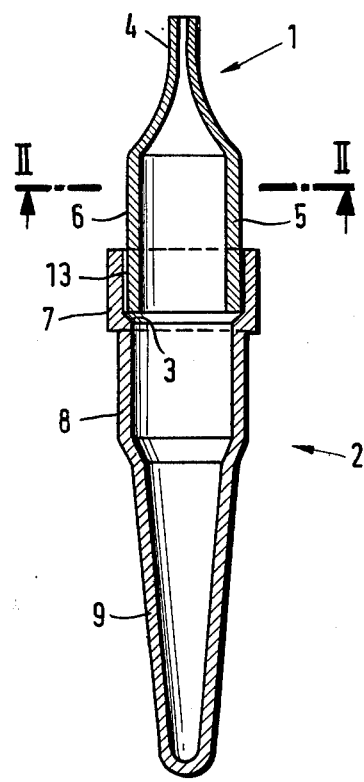
FIG. 1 is an enlarged cross-sectional view of a capillary receptacle according to the invention.
Figure 2:
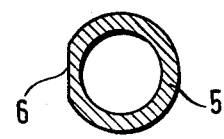
FIG. 2 is a sectional view taken along line II—II of FIG. 1.
Figure 3:
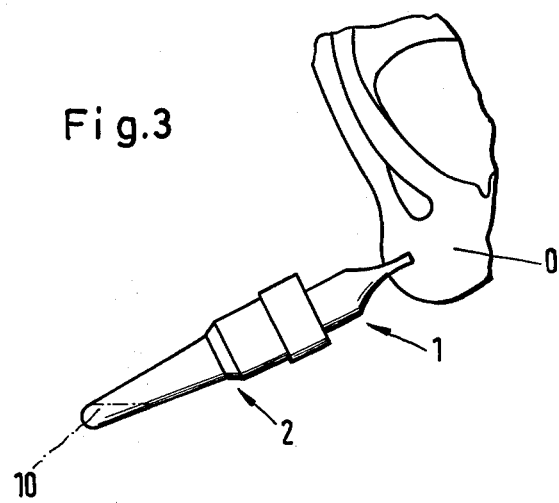
FIG. 3 is an elevational view in a true scale of a capillary receptacle applied to the lobe of the ear of a patient.

The capillary receptacle according to FIGS. 1 to 3 comprises a receiving receptacle 2 and a plugged-in insert 1. The insert is tapered funnel-shaped at its upper end and opens into a very short capillary 4. In the preferred embodiment capillary 4 has a length of 1–3 mm, preferably 2 mm. Capillary 4, as illustrated in FIG. 3, is applied to the injection site in a lobe 0 of an ear (or into a finger tip or the like). The main portion 5 of the insert is, as will be noted from FIG. 2, generally formed circular-cylindrical, but provided with a flattened portion 6 on one side which upon inserting the insert into the opening portion 7 of the receiving receptacle 2 results in a venting duct 13 between these portions by which air displaced when blood flows in is able to escape.

The receiving receptacle is slightly tapered in its bottom portion 9 and thus permits a storing and good handability of even minimum quantities of blood. Adjacent to this tapered bottom portion, there is provided a circular-cylindrical upper portion 8 which permits the storing of even major quantities of blood. This upper portion finally merges into an enlarged opening portion 7 which tightly receives the main portion 5 of the insert. The cylindrical inner wall of this opening portion 7 merges into the narrower inner wall of the upper portion 8 through the intermediary of a tapered portion 3 on which the bottom edge of the main portion 5 of the insert 1 rests.

When the capillary tip 4 of the insert, as illustrated in FIG. 3, is applied to the point of injection at a lobe of an ear or a finger tip, the outflowing blood is drawn in by the capillary. The capillary receptacle on the whole is held slightly downwardly inclined. The result thereof is that the blood drawn in initially by the capillary action into the tip 4 then flows into the enlarged portion of the insert subject to the action of gravity, detaches from the wall there and continues to flow on. From the lower edge of the insert which is dimensioned a little narrower than the inner wall of the upper portion of the receiving receptacle the blood then flows further downwardly into the receiving receptacle and collects at the bottom thereof, as indicated at 10 in FIG. 3. The blood flows from the point of injection into the receiving receptacle as long as the capillary 4 stays immerged in the liquid blood.

In order to prevent a coagulation of the extracted blood, in a manner known per se an anti-coagulant substance may be introduced into the receiving receptacle 2.

Figure 4:
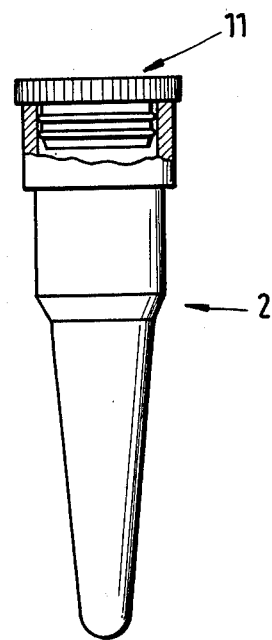
FIG. 4 is a partially broken-away elevational view of the receptacle of the capillary receptacle of FIGS. 1 and 2, closed by a plug.

After effecting removal of the desired quantity of blood, the insert is withdrawn and discarded, and the receiving receptacle is closed by a plug 11, as illustrated in FIG. 4. The blood may now be centrifugalized in this receptacle or also tested directly.

Figure 5:
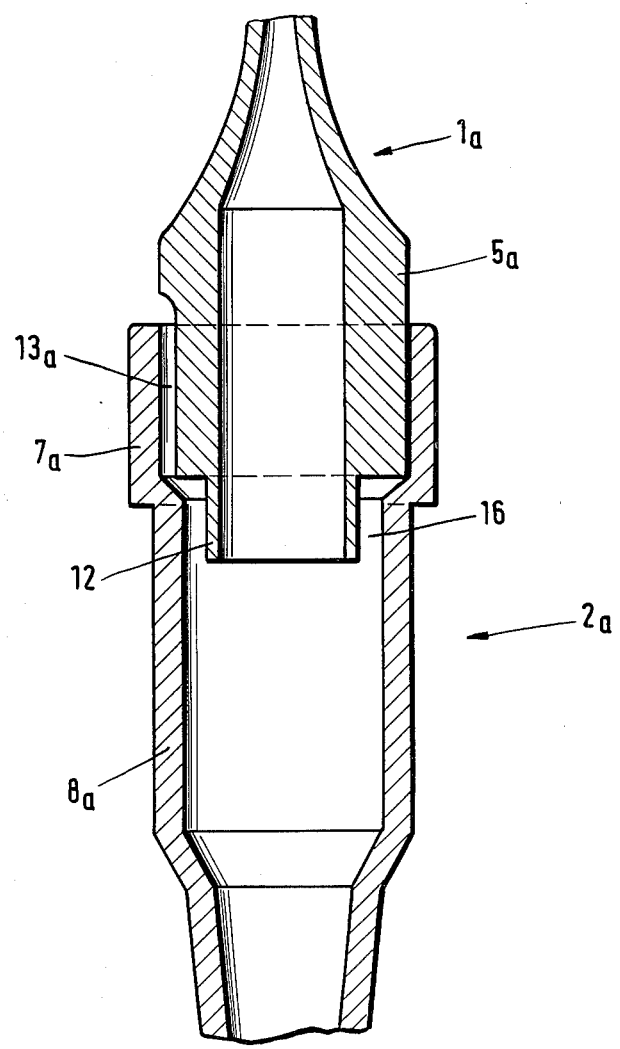
FIG. 5 is a more enlarged part-sectional view of a modified embodiment.

In the embodiment illustrated in FIG. 5, the receiving receptacle 2a is virtually unmodified, whereas the main portion 5a of the insert 1a extends with its lower, offset end 12 into the upper portion 8a of the receiving receptacle 2a. The cylindrical inner wall of the main portion 5a of the insert 1a extends smoothly and without any shoulder, so that the inflowing blood is able to smoothly flow off. The tapered end 12 is only dimensioned so thick externally that between it and the surrounding upper portion 8a of the receiving receptacle a gap of such a size remains that it has no capillary effect and the blood is able to flow off unobstructed.

Figure 6:
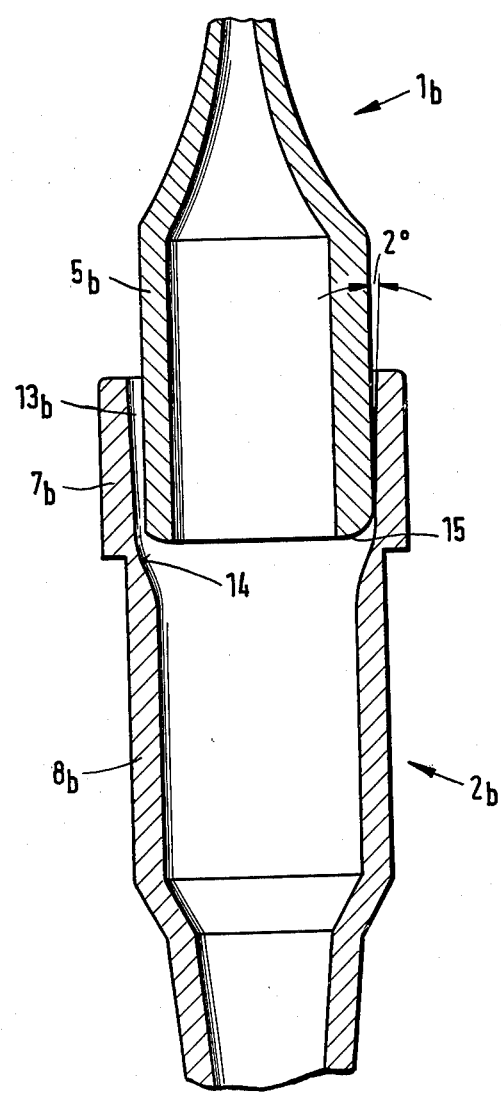
FIG. 6 is a likewise more enlarged part-sectional view of a further embodiment of the invention.

In the embodiment illustrated in FIG. 6, the inner wall of the opening portion 7b of the receiving receptacle 2a is enlarged slightly tapering toward the opening, in this embodiment by way of example by 2°. The main portion 5b of the insert 1b is formed circular-cylindrical like in the embodiments described hereinbefore and rounded at its lower end at 15. The dimensions are such that the insert 1b is able to be clampingly inserted into the opening portion provided with a tapering opening.

Since in this embodiment no inner shoulder is required anymore at the location of transition from the opening portion to the upper portion of the receiving receptacle for supporting the lower edge of the insert, the slightly tapered inner wall of the opening portion here gradually and without any sharp edges merges at 14 into the cylindrical inner wall of the upper portion 8b. Thereby, again a non-obstructed flowing-off of the extracted blood is permitted.

Figure 7:
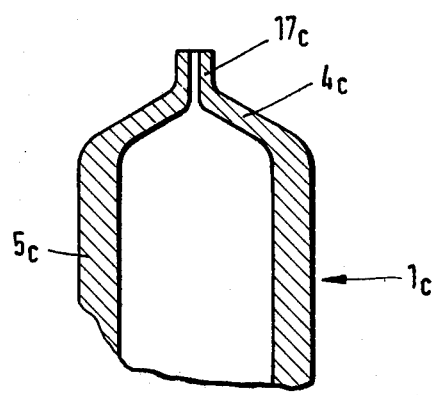
FIG. 7 is a part-sectional view at the same scale as the illustrations of FIGS. 5 and 6, of a modified insert.

In the embodiment illustrated in FIG. 7, the tip 17c of the insert 1c is dimensioned only very short, namely so short that a capillary suction effect just exists. Between this tip 17c and the main portion 5c of the insert, there is a steep, funnel-shaped portion 4c. This steep configuration of the funnel in relationship to the slender configuration of the preceding figures brings about the advantage that the blood drawn through the tip immediately upon entering the funnel is torn off the wall and flows off downwardly into the receiving receptacle subject to the effect of gravity non-obstructed via the lower positioned portion of the side wall 5c.

Figure 8:
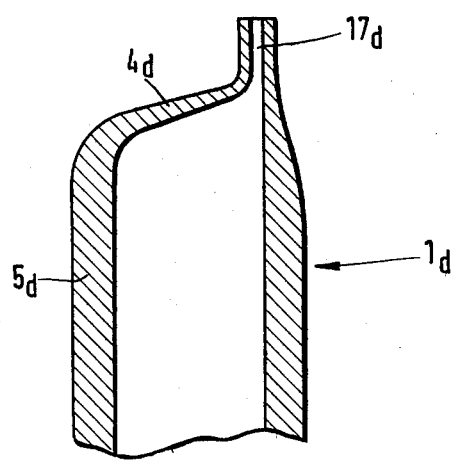
FIG. 8 is a part-sectional view at the same scale of an insert provided with an eccentrical arrangement of the tip.

In the embodiment illustrated in FIG. 8, of the insert 1d, the tip 17d is arranged eccentrically and possesses a common tangential plane with the portion of the inner wall of the main portion 5d adjacent thereto. Upon extraction of blood from the point of injection, the insert is then held in such a way that the blood drawn by the capillary is able to flow off non-obstructedly. According to the eccentric position of the tip 17d, the funnel-shaped portion 4d between this tip and the main portion is also formed eccentrically.

The flattened portion illustrated in FIGS. 1, 5 and 6 at one side of the insert for the sake of simplicity has not been illustrated in FIGS. 7 and 8 for these embodiments and may be positioned underneath the break-away position of these figures, respectively.

I claim:

1. A capillary receptacle for the extraction and storage of blood, comprising:
 a receiving receptacle having a bottom portion slightly tapering inwardly toward a closed bottom, said tapered portion extending over a substantial portion of the length of the receiving receptacle and defining a tapered receiving chamber, a cylindrical upper portion adjacent to the bottom portion, and a substantially cylindrical top portion, having a larger inner diameter than that of said upper portion, adjacent to the cylindrical upper portion and open at the upper end thereof; and
 a removable insert having a cylindrical main portion, inserted into the top portion of said receiving receptacle, and a short portion, the interior of which is funnel shaped, adjacent to the cylindrical main portion, the tip of the short portion having such a small inner diameter that blood externally thereof is drawn in by capillary action and the main portion of said insert having such a large inner diameter that the entering blood is able to freely flow onto and off therefrom into said receiving receptacle without being hindered by capillary action; and
 wherein the outside of the cylindrical main portion of said insert and the inside diameter of the top portion of said receiving receptacle are so shaped that the outside of the cylindrical main portion is tightly received into the inside of said top portion with a venting duct provided therebetween.

2. A capillary receptacle according to claim 1, wherein the tip of the funnel-shaped portion of said insert has a length of 1 to 3 mms.

3. A capillary receptacle according to claim 1, wherein the venting duct is formed by a flattened portion on the external circumference of the main portion of said insert.

4. A capillary receptacle according to claim 1, wherein the inner diameter of the main portion of said insert is smaller than that of the cylindrical upper portion of said receiving receptacle.

5. A capillary receptacle according to claim 1, wherein the external diameter of the end of the main portion of said insert extending into the cylindrical upper portion of said receiving receptacle, defines with the inner wall of said cylindrical upper portion a spacing gap which is so small that no capillary effect occurs and blood is able to flow off unobstructed.

6. A capillary receptacle according to claim 1, wherein a plug is provided associated with the receiving receptacle for closing it.

7. A capillary receptacle according to claim 1, wherein the funnel-shaped portion of said insert is formed eccentrical relative to the main portion of said insert and the capillary bore in the tip is disposed at the outer edge of the bore of said main portion.

8. A capillary receptacle according to claim 1, wherein the tip of the funnel-shaped portion of said insert has a length of 2 mms.

9. A capillary receptacle according to claim 1, wherein the top portion of said receiving receptacle enlarges toward its open upper end, slightly tapered, and the external diameter of the main portion of said insert is dimensioned and rounded at the lower edge thereof, said insert being so shaped and dimensioned that it can be clampingly inserted into said top portion of said receiving receptacle.

10. A capillary receptacle according to claim 9, wherein the slightly tapered inner wall of the top portion of said receiving receptacle gradually and without any sharp edges merges into the cylindrical inner wall of the cylindrical upper portion thereof, and wherein said receiving receptacle is rounded at its lower end.

11. A capillary receptacle according to claim 9, wherein the slightly tapered receptacle of the top portion of said receiving receptacle gradually and without any sharp edges merges into the cylindrical inner wall of the cylindrical upper portion of said receiving receptacle.

* * * * *